United States Patent
Zai et al.

(10) Patent No.: US 10,301,678 B2
(45) Date of Patent: May 28, 2019

(54) GENETIC MARKERS FOR ANTIPSYCHOTIC INDUCED WEIGHT GAIN AND METHODS FOR USE THEREOF

(71) Applicant: Centre for Addiction and Mental Health, Toronto (CA)

(72) Inventors: Clement C. Zai, Toronto (CA); James L. Kennedy, Toronto (CA); Daniel J. Mueller, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 279 days.

(21) Appl. No.: 15/029,955

(22) PCT Filed: Oct. 17, 2014

(86) PCT No.: PCT/CA2014/051000
§ 371 (c)(1),
(2) Date: Apr. 15, 2016

(87) PCT Pub. No.: WO2015/054792
PCT Pub. Date: Apr. 23, 2015

(65) Prior Publication Data
US 2016/0237499 A1    Aug. 18, 2016

Related U.S. Application Data

(60) Provisional application No. 61/892,094, filed on Oct. 17, 2013.

(51) Int. Cl.
*C12Q 1/68* (2018.01)
*C12Q 1/6883* (2018.01)
*A61K 31/5513* (2006.01)

(52) U.S. Cl.
CPC ........ *C12Q 1/6883* (2013.01); *A61K 31/5513* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,210,015 | A | 5/1993 | Gelfand et al. |
| 5,487,972 | A | 1/1996 | Gelfand et al. |
| 7,795,033 | B2 | 9/2010 | McMahon et al. |
| 8,012,718 | B2 | 9/2011 | Ruano et al. |
| 8,355,927 | B2 | 1/2013 | Lombard |
| 8,389,247 | B2 | 3/2013 | Ruano et al. |
| 8,476,012 | B2 | 7/2013 | Ruano et al. |
| 2009/0075254 | A1 | 3/2009 | Ruano et al. |
| 2009/0263814 | A1 | 10/2009 | Ruano et al. |
| 2011/0312508 | A1 | 12/2011 | Ruano et al. |

FOREIGN PATENT DOCUMENTS

| | | |
|---|---|---|
| WO | WO-95/13399 A1 | 5/1995 |
| WO | WO-03/039234 A2 | 5/2003 |
| WO | WO-03/039234 A3 | 5/2003 |
| WO | WO-2013/088135 A1 | 6/2013 |

OTHER PUBLICATIONS

Enoch et al; Neuropsychopharmacology; vol. 34, pp. 1245-1254, 2009.*
International Search Report Issued in PCT/CA2014/051000 dated Jan. 12, 2015.
Bauer, L.O. et al. "GABRA2 genotype, impulsivity and body mass" (2012). Am. J. Addict 21:404-410.
Bauer, L. et al. "Obesity, smoking and frontal brain dysfunction" (2010). Am. J. Addict. 19:397-400.
Edenberg, H.J. et al. "Variations in GABRA2, encoding the a3 subunit of the GABAa receptor, are associated with alcohol dependence and with brain oscillations" (2004). Am. J. Hum. Genet. 74:705-714.
Villafuerte, S. et al. "Impulsiveness mediates the association between GABRA2 SNPs and lifetime alcohol problems" Jul. 2013 (Jul. 2013). Genes Brain Behav, 12:525-531.
Arranz, M.J. et al. (Aug. 2007, e-published Jun. 5, 2007). "Pharmacogenetics and pharmacogenomics of schizophrenia: a review of last decade of research," *Mol Psychiatry* 12(8): 707-747.
Chowdhury, N.I. et al. (Jun. 2013, e-published Feb. 7, 2012). "Genetic association study between antipsychotic-induced weight gain and the melanocortin-4 receptor gene," *Pharmacogenomics J* 13(3):272-279.
Cooper, S.J. (Apr. 2005). "Palatability-dependent appetite and benzodiazepines: new directions from the pharmacology of GABA(A) receptor subtypes," *Appetite* 44(2): 133-150.
Danovich. L. et al. (Mar. 2011, e-published Febraury 25, 2010). "The involvement of GABA(A) receptor in the molecular mechanisms of combined selective serotonin reuptake inhibitor-antipsychotic treatment," *Int J Neuropsychopharmacol* 14(2): 143-155.
De Hert M. et al. (Sep. 1, 2012). "Body weight and metabolic adverse effects of asenapine, iloperidone, lurasidone and paliperidone in the treatment of schizophrenia and bipolar disorder: a systematic review and exploratory meta-analysis," *CNS Drugs* 26(9):733-759.
Drew, K.L. et al. (Oct. 23, 1990). "Regional specific effects of clozapine and haloperidol on GABA and dopamine release in rat basal ganglia," *Eur J Pharmacol* 187(3): 385-397.

(Continued)

*Primary Examiner* — Jehanne S Sitton
(74) *Attorney, Agent, or Firm* — Muriel Liberto, Esq.; Mintz Levin Cohn Ferris Glovsky and Popeo, P.C.

(57) ABSTRACT

Provided is a method of predicting a subject's weight response to antipsychotic drug treatment by obtaining a biological sample comprising genomic DNA from the subject and determining the presence or absence of one or more polymorphisms in the GABRA2 gene of the subject, wherein the presence of said one or more polymorphisms is predictive of the subject's weight change in response to antipsychotic drug treatment. The method also may comprise additional steps including treating the subject. Kits and components thereof are also provided.

9 Claims, No Drawings

Specification includes a Sequence Listing.

(56) References Cited

OTHER PUBLICATIONS

Duke, A.N. et al. (Aug. 2006, e-published Jun. 17, 2006). "Enhanced sucrose pellet consumption induced by benzodiazepine-type drugs in squirrel monkeys: role of GABAA receptor subtypes," *Psychopharmacology* (Berl):187(3): 321-330.

Ebenezer, I.S. et al (Aug. 13, 2007, e-published Jun. 5, 2007). "The effects of intraperitoneal administration of the GABA(B) receptor agonist baclofen on food intake in CFLP and C57BL/6 mice," *Eur J Pharmacol* 569(1-2): 90-93.

Gebhardt, S. et al. (2010). "Body weight gain induced by atypical antipsychotics: an extension of the monozygotic twin and sib pair study," *J Clin Pharm Ther* 35(2): 207-211.

Kane, J.M. et al. (1988). "Clozapine in treatment-resistant schizophrenics," *Psychopharmacol Bull* 24(1): 62-67.

Lett, T.A. et al. (Mar. 2012, e-published Sep. 6, 2011). "Pharmacogenetics of antipsychotic-induced weight gain: review and clinical implications," *Mol Psychiatry* 17(3):242-266.

Marx, C.E. et al. (2003). "Olanzapine and clozapine increase the GABAergic neuroactive steroid allopregnanolone in rodents," *Neuropsychopharmacology* 28(1):1-13.

Masellis, M. et al. (Aug. 1998). "Serotonin subtype 2 receptor genes and clinical response to clozapine in schizophrenia patients," *Neuropsychopharmacology* 19(2): 123-132.

Müller, D.J. et al. (Sep. 2006). "Genetics of antipsychotic treatment emergent weight gain in schizophrenia," *Pharmacogenomics* 7(6): 863-887.

Müller, D.J. et al. (Apr. 2012, e-published Aug. 17, 2010). "Systematic analysis of dopamine receptor genes (DRD1-DRD5) in antipsychotic-induced weight gain," *Pharmacogenomics J* 12(2):156-164.

Tiwari, A.K. et al. (Dec. 1, 2010, e-published Aug. 20, 2010). "Association study of polymorphisms in cholecystokinin gene and its receptors with antipsychotic induced weight gain in schizophrenia patients," *Prog Neuropsychopharmacol Biol Psychiatry* 34(8):1484-1490.

Vincent, S.L. al. (May 1994). "The effects of chronic haloperidol administration on GABA-immunoreactive axon terminals in rat medial prefrontal cortex," *Synapse* 17(1):26-35.

Weston-Green, K. et al. (Mar. 16, 2012). "Alterations to Melanocortinergic, GABAergic and Cannabinoid Neurotransmission Associated with Olanzapine-Induced Weight Gain," *PLoS One* 7(3): e33548.

Willer, C.J. et al. (Jan. 2009, e-published Dec. 14, 2008). "Six new loci associated with body mass index highlight a neuronal influence on body weight regulation," *Nat Genet* 41(1): 25-34.

Zai, G.C. et al. (Oct. 1, 2012, e-published May 27, 2012). "The role of brain-derived neurotrophic factor (BDNF) gene variants in antipsychotic response and antipsychotic-induced weight gain," *Prog Neuropsychopharmacol Biol Psychiatry* 39(1): 96-101.

Brandl, E.J. et al. (Aug. 7, 2012, e-published Mar. 8, 2012). "Association study of polymorphisms in leptin and leptin receptor genes with antipsychotic-induced body weight gain," *Prog Neuropsychopharmacol Biol Psychiatry* 38(2):134-141.

Czerwensky, F. et al. (Oct. 2013, e-published Aug. 7, 2013). "MC4R rs489693: a clinical risk factor for second generation antipsychotic-related weight gain?" *Int J Neuropsychopharmacol* 16(9):2103-2109.

Souza, R.P. et al. (Apr. 2012, e-published Feb. 2, 2012). "Association study between variants of AMP-activated protein kinase catalytic and regulatory subunit genes with antipsychotic-induced weight gain," *J Psychiatr Res* 46(4):462-468.

Villafuerte, S. et al. (Mar. 2013). "Impulsiveness mediates the association between GABRA2 SNPs and lifetime alcohol problems," *Genes, Brain and Behavior* 12:525-231.

Edenberg, H.J. et al. (Feb. 2004). "Variations in GABRA2, encoding the a2 subunit of the $GABA_A$ receptor, are associated with alcohol dependence and with brain oscillations," *Am J. Hum. Genet.* 74:705-714.

Bauer, L.O. et al. (2012). "GABRA2 genotype, impulsivity, and body mass," *Am. J. Addict.* 21(5):404-410.

* cited by examiner

GENETIC MARKERS FOR ANTIPSYCHOTIC INDUCED WEIGHT GAIN AND METHODS FOR USE THEREOF

RELATED APPLICATIONS

This application is a national stage application, filed under 35 U.S.C. § 371, of International Application No. PCT/CA2014/051000, filed on Oct. 17, 2014, which claims priority to U.S. Provisional Patent Application No. 61/892,094 filed on Oct. 17, 2013, the contents of which are hereby fully incorporated by reference.

FIELD OF INVENTION

The present invention relates to the use of genetic markers. More specifically, the present invention relates to genetic markers in GABRA2 that are associated with antipsychotic induced weight gain and use thereof.

BACKGROUND OF THE INVENTION

Treatment of psychosis symptoms, for example schizophrenia (SCZ) symptoms with antipsychotics has been limited by poor efficacy and adverse reactions. This is especially true for second-generation antipsychotics, such as clozapine and olanzapine, where about 30% of treated patients experience significant weight gain. Antipsychotics are used to treat psychotic symptoms that are commonly observed in schizophrenia, bipolar disorder, and psychotic depression. They have been used increasingly to manage other psychiatric disorders, including bipolar manic and mixed episodes[1], major depressive disorder[2,3], autistic spectrum disorder[4,5], general anxiety disorder, obsessive-compulsive disorder, dementia[6-8].

While the underlying mechanisms of antipsychotic response and adverse effects remain unclear, genetic factors appear to play a prominent role[9-14].

There is increasing evidence for a role of gamma-aminobutyric acid (GABA) in the regulation of food intake. GABA is produced in many regions of the brain, including the (proopiomelanocortin) POMC and Agouti-related peptide (AGRP) neurons in the hypothalamus[15,16]. Diphtheria toxin-mediated ablation of GABA-secreting AGRP neurons induced an anorexic phenotype in mice (reviewed in[17]). Similarly, mice genetically deficient in GABA release from AGRP neurons were resistant to obesity induced by ghrelin[18]. The mechanism of this resistance could be through a decrease in food intake and an increase in energy expenditure in these AGRP GABA-deficient mice[18]. Conversely, administration of GABA agonists, including the benzodiazepine midazolam and L-838417, into the parabrachial nucleus in the brainstem, increased food intake[19]. Both $GABA_A$ and $GABA_B$ receptor agonists enhanced feeding in rodents and other animal models[20-22]. The GABRA2 gene, in particular, was one of the top findings in a recent genome-wide meta-analysis of obesity[23], making it an appealing candidate gene for further investigation in obesity and related phenotypes.

There is also accumulating evidence for alterations in GABA neurotransmission by various antipsychotic drugs[24-26]. Clozapine and olanzapine, in particular, may exert their anxiolytic activity by increasing GABA-ergic neurotransmission[27] through the allosteric action of neuroactive steroids including allopregnanolone at the $GABA_A$ receptor[28]. Olanzapine-induced weight gain and adiposity has been correlated to increased levels of the GABA synthesis enzyme GAD65[29].

The GABRA2 gene (HGNC:4076), which is mapped to chromosomal region 4p12, codes for the $GABA_A$ receptor, alpha 2 subunit. While the GABRA2 gene was implicated in obesity[23], it has not been investigated in relation to antipsychotic induced weight gain.

There is a need in the art for novel genetic markers. Further, there is a need in the art for novel genetic markers associated with antipsychotic-induced weight gain. Further, there is a need in the art for genetic diagnostic markers for antipsychotic-induced weight gain that provide physicians and other health care professionals with the opportunity to generate educated decisions for prescribing medications for treatment of psychosis. Moreover, there is a need in the art for personalized medicine approaches that lower the risk of developing antipsychotic induced weight gain and related ailments such diabetes and cardiovascular disease.

SUMMARY OF THE INVENTION

The present invention relates to genetic markers. More specifically, the present invention relates to genetic markers in GABRA2 that are associated with antipsychotic induced weight gain and use thereof.

As a convention, all references to nucleotide sequences herein are recited with respect to the positive strand. As will be understood by a person of skill in the art, GABRA2 gene is transcribed off the negative strand. Thus it is fully contemplated that the subject matter herein may be practiced as outlined as recited or it may be practiced by employing/determining/analyzing the complement of the nucleotide sequences recited herein.

The following nucleotide sequences were examined in this study. The polymorphic sites are shown underlined in bold:

a) rs16859227

(SEQ ID NO: 1)
CCTTGGTTTTATACAAGCATGCAAAG[C/T]ATATAATAGAATCACA
TGGAAACAA, b) rs279858

(SEQ ID NO: 2)
ATTGTCATATTATGAGCTACTGATTT[T/C]TTCCCATTGTGAAAAA
AGGTATCTG;

c) rs1442060

(SEQ ID NO: 3)
GTAAAGTGTCACATCAATGCCATATC[A/G]TATTCTGTAGATGGCA
TGTTATCAT, d) rs3849591

(SEQ ID NO: 4)
CTCATTTCCTTGCTTCTAAGGTAGGG[G/T]TCATCAATTTATCTAT
CTCATGGGA, e) rs1442062

(SEQ ID NO: 5)
GAGAAGGTGAAATAGATTTAACTCAT[A/G]TATCAAATTAAGATTG
CACCTTAAA, f) rs16859354

(SEQ ID NO: 6)
TACAATATCTTGACTCAATGAGCTTC[G/T]AATCTTAATAAGGTAA
CAAGAGAAA, g) rs11503014

(SEQ ID NO: 7)
AAGCTATGGAGATTACTTCCTGGACT[C/G]TGTGTAGGACTTGATG
ATTGAGAGA,

-continued h) rs6856130

(SEQ ID NO: 8)
TCTGTTCTGTTTTATCTGAGGCGATA[A/G]AATCCAAACGTGCAAC
TTGAACAAC,
or i) rs1372472

(SEQ ID NO: 9)
ATAAAACTCTGGTAATTCAAACCAAA[A/T]ATTTCCTCACTGAAAA
CTATGCTTG.

According to the present invention there is provided a method of predicting a subject's weight change in response to antipsychotic drug treatment comprising,
a) obtaining a biological sample comprising genomic DNA from the subject;
b) determining the presence or absence of one or more polymorphisms in the GABRA2 gene of the subject, wherein the presence of said one or more polymorphisms is predictive of the subject's weight change in response to antipsychotic drug treatment.

In a further embodiment, there is provided a method as described above, further comprising at least one step selected from the group consisting of a) treating the subject with one or more therapeutics based on the results obtained from said determining the presence or absence of one or more polymorphisms in the GABRA2 gene b) advising and/or counseling the subject with respect to the results of determining the presence or absence of one or more polymorphisms in the GABRA2 gene; c) transmitting, advising and/or conveying the results to a physician, medical service provider or other third party; d) treating the subject with one or more particular antipsychotic treatment(s) based on the results; e) treating the subject prior to, concurrently with or after antipsychotic treatment with one or more therapies or therapeutics to control weight gain; f) monitoring the subject's weight over a period of time; g) prescribing, recommending or subjecting the patient or subject to exercise or diet changes; h) monitoring the subject for metabolic syndrome, i) monitoring the subject for cardiovascular disease or symptoms thereof, or any combination of a-i).

Also provided by the present invention is a method as described above, wherein the subject has been diagnosed with schizophrenia or schizoaffective disorder, is likely to develop schizophrenia or schizoaffective disorder, or exhibits one or more symptoms of schizophrenia or schizoaffective disorder. In a further embodiment, which is not meant to be limiting in any manner, it is also contemplated that the subject has not yet been diagnosed with schizophrenia or schizoaffective disorder before the method as described herein is performed.

According to a further embodiment, there is provided a method as described above wherein the one or more polymorphisms in the GABRA2 gene are relative to:

a) rs16859227

(SEQ ID NO: 1)
CCTTGGTTTTATACAAGCATGCAAAG[C/T]ATATAATAGAATCACA
TGGAAACAA,
or b) rs279858

(SEQ ID NO: 2)
ATTGTCATATTATGAGCTACTGATTT[T/C]TTCCCATTGTGAAAAA
AGGTATCTG;

wherein the polymorphic site is in brackets, underlined and in bold.

In a further embodiment, there is provided a method as described above, wherein at least one of the polymorphisms is defined by SEQ ID NO:1 or a variant or fragment thereof comprising the polymorphic site. As indicated previously, the method also may be practiced by determining the presence or absence of the complement of the nucleotide sequence defined by SEQ ID NO:1 including the complement of the polymorphic site.

In a further embodiment, there is provided a method as described above, wherein at least one of the polymorphisms is defined by SEQ ID NO:2 or a variant or fragment thereof comprising the polymorphic site. As indicated previously, the method also may be practiced by determining the presence or absence of the complement of the nucleotide sequence defined by SEQ ID NO:2 including the complement of the polymorphic site.

Also provided is a method as defined above, wherein the presence of the C allele (C/C genotype) of the rs16859227 polymorphism (SEQ ID NO:1) is associated with a higher percentage weight gain in subjects. Also provided is a method as defined above, wherein the presence of two copies of the T allele (T/T genotype) of the rs279858 polymorphism (SEQ ID NO: 2) is associated with a higher percentage weight gain in subjects.

Also provided is a method as described above, wherein the sample is a blood sample.

Further provided is a kit comprising one or more of the following:
a) one or more primers to amplify a nucleotide sequence that comprises the polymorphism as defined in SEQ ID NOs:1-9, or a combination thereof;
b) one or more probes that hybridize to any one of SEQ ID NOs:1-9, over a region of nucleotides comprising the polymorphic site, wherein said probe hybridizes to a particular variant of the polymorphisms shown at the polymorphic site. Without wishing to be limiting in any manner, the probes may be labeled with an appropriate group, for example, a fluorescent tag, fluorophore, radioactive label or the like. Further, the one or more probes may be attached covalently or physically associated with a support for example, but not limited to a biochip, array, slide, multiwell plate, bead or the like. In an embodiment, which is not meant to be limiting in any manner, the probes may comprise an array of nucleic acids.
c) one or more reagents and/or products including, but not limited to, one or more buffers for performing PCR or probe hybridization, or any step in such as process as would be known to a person of skill in the art, one or more DNA amplifying enzymes, or any combination thereof
d) one or more reagents, components and products for genotyping the polymorphisms as described herein, including, but not limited to those used in exonuclease assays, nucleotide sequencing, or any combination thereof;
e) one or more reagents, components or products for performing a DNA sequencing reaction that determines the sequence of a nucleotide sequence comprising any one of SEQ ID NOs: 1-9 or a combination thereof, and;
f) one or more sets of instructions for using the components as described herein, practicing the methods of the present invention as described herein, interpreting the data obtained from practicing the methods of the present invention or any combination thereof.

This summary of the invention does not necessarily describe all features of the invention.

DETAILED DESCRIPTION

The following description is of an illustrative embodiment.

The present invention provides genetic markers that can be used to predict a subject's susceptibility to weight change in response to antipsychotic drug therapy. As described in more detail below, specific polymorphisms in the GABRA2 gene may be used to predict a subject's weight change in response to antipsychotic drug therapy. In a second embodiment, specific polymorphisms in the GABRA2 gene may be used to assist in determining a treatment regimen for a subject diagnosed with schizophrenia or for a subject likely of developing schizophrenia. In a third embodiment, specific polymorphisms in the GABRA2 gene may be used in treating a schizophrenic subject. In a fourth embodiment, there is provided a method of treating a subject with antipsychotic medication, wherein the method comprises identifying one or more specific polymorphisms in the GABRA2 gene as part of the treatment regimen. Other embodiments are also provided as described herein.

The study described in the examples and as referred to herein and throughout investigated the effect of single nucleotide polymorphisms (SNPs) across the GABRA2 gene on weight response to antipsychotic medication in multiple distinct schizophrenic populations. The subjects included 160 patients of European ancestry with DSM-IIIR/IV diagnoses of schizophrenia or schizoaffective disorder. Results indicate that the T/T genotype of the rs279858 marker was associated with a higher percent weight change than the C-allele carrying genotypes (for example, either the T/C or C/C genotypes). The rs16859227 marker was also significantly associated with higher percent weight change in a subsample of schizophrenia or schizoaffective disorder subjects who were on clozapine or olanzapine medication. Results indicate that the C/C genotype of the rs16859227 marker was associated with a higher percent weight change than the T-allele carrying genotypes (for example, either the T/T or T/C genotypes). Other interesting results are also provided herein, particularly Tables 1 and 2.

According to an embodiment of the present invention, there is provided a method of predicting a subject's weight change in response to antipsychotic drug treatment comprising,
 a) obtaining a biological sample comprising genomic DNA from the subject;
 b) determining the presence or absence of one or more polymorphisms in the GABRA2 gene of the subject, wherein the presence of said one or more polymorphisms is predictive of the subject's susceptibility to weight change in response to antipsychotic drug treatment.

In a further embodiment, which is not meant to be limiting in any manner, the method may comprise one or more additional steps, for example, but not limited to advising and/or counseling the subject with respect to the results of determining the presence or absence of one or more polymorphisms in the GABRA2 gene; transmitting, advising and/or conveying the results to a physician, medical service provider or other third party; treating the subject with one or more particular antipsychotic treatment(s) based on the results; treating the subject prior to, concurrently with or after antipsychotic treatment with one or more therapies to control weight gain; monitoring the subject's weight over a period of time, monitoring the subject for metabolic syndrome or the development of metabolic syndrome which may include measuring blood lipid profiles, including triglycerol and triglycerides, blood glucose levels, body mass index (BMI) and central obesity. As cardiovascular disease may result from metabolic syndrome, clinicians may also monitor for the development of heart disease. The following symptoms of heart disease may be monitored including elevated blood pressure, angina, heart failure, shortness of breath, rapid or irregular pulse, coughing and nausea, or any combination of the above. Based on the test, if for example a SCZ subject exhibits the T/T genotype for the rs279858 marker, more frequent weight monitoring as well as the administration of an appetite suppressant or hypoglycemic drug, for example, but not limited to a sulfonylurea, thiazolidinedione, alpha glucosidase inhibitor, or metformin, a diet plan, an exercise regime, or their combinations in addition to antipsychotic medication may be recommended. Also, from the results provided, subjects exhibiting the T/T genotype for the rs279858 marker preferably are not treated with second generation antipsychotics (especially those with higher propensity for weight gain: for example, clozapine, olanzapine) but should rather be treated with antipsychotics with lower propensity for weight gain[30] (including fluphenazine, aripiprazole, ziprasidone, haloperidol, loxapine, lurasidone, iloperidone, asenapine and molindone).

Thus, based on the genotype of the patient, a physician may wish to avoid the prescription of antipsychotics that cause high or the highest level of weight gain, these include: olanzapine and clozapine. Moderate risk medications such as paliperidone, perphenazine, thioridazine, chlorpromazine, risperidone and quetiapine may be prescribed with more frequent monitoring of metabolic syndrome and heart disease indices. Lastly, a physician may wish to choose a lower risk drug for induced weight gain, these drugs include: loxapine, iloperidone, asenapine, lurasidone, ziprasidone, aripiprazole, fluphenazine, and haloperidol.

As described above, but without wishing to be considered limiting, specific polymorphisms in the GABRA2 gene may be used to assist in determining a treatment regimen for a subject diagnosed with schizophrenia (or schizoaffective disorder) or likely of developing schizophrenia (or schizoaffective disorder). For example, but not wishing to be considered limiting in any manner, the present invention provides a method of determining a treatment regimen for a subject diagnosed with schizophrenia or likely of developing schizophrenia comprising,
 a) obtaining a biological sample comprising genomic DNA from the subject;
 b) determining the presence or absence of one or more polymorphisms in the GABRA2 gene of the subject, wherein the presence of said one or more polymorphisms is predictive of the subject's weight change in response to antipsychotic drug treatment, wherein
 the presence of one or more GABRA2 polymorphisms as described herein and/or the absence of one or more GABRA2 polymorphisms as described herein define a treatment regimen for the subject.

In such an embodiment, the method may further comprise a step of treating the subject as described above, below or anywhere herein.

Further, as described above, specific polymorphisms in the GABRA2 gene may be used in treating a schizophrenic subject or how to treat a subject that may be predisposed to schizophrenia. In such an embodiment, the present invention provides a method of treating a schizophrenic subject or a subject that may be predisposed to schizophrenia comprising,
 a) obtaining a biological sample comprising genomic DNA from the subject;

b) determining the presence or absence of one or more polymorphisms in the GABRA2 gene of the subject, wherein the presence of said one or more polymorphisms is predictive of the subject's weight change in response to antipsychotic drug treatment, wherein the presence of one or more GABRA2 polymorphisms as described herein and/or the absence of one or more GABRA2 polymorphisms as described herein define a treatment regimen for the subject.

In such an embodiment, the method may further comprise a step of treating the subject as described above or anywhere herein.

By the term "one or more polymorphisms in the GABRA2 gene" it is meant one or more polymorphisms in the nucleotide sequences as defined by:

a) rs16859227

(SEQ ID NO: 1)
CCTTGGTTTTATACAAGCATGCAAAG[C/T]ATATAATAGAATCACA
TGGAAACAA b) rs279858

(SEQ ID NO: 2)
ATTGTCATATTATGAGCTACTGATTT[T/C]TTCCCATTGTGAAAAA
AGGTATCTG c) rs1442060

(SEQ ID NO: 3)
GTAAAGTGTCACATCAATGCCATATC[A/G]TATTCTGTAGATGGCA
TGTTATCAT, d) rs3849591

(SEQ ID NO: 4)
CTCATTTCCTTGCTTCTAAGGTAGGG[G/T]TCATCAATTTATCTAT
CTCATGGGA, e) rs1442062

(SEQ ID NO: 5)
GAGAAGGTGAAATAGATTTAACTCAT[A/G]TATCAAATTAAGATTG
CACCTTAAA, f) rs16859354

(SEQ ID NO: 6)
TACAATATCTTGACTCAATGAGCTTC[G/T]AATCTTAATAAGGTAA
CAAGAGAAA, g) rs11503014

(SEQ ID NO: 7)
AAGCTATGGAGATTACTTCCTGGACT[C/G]TGTGTAGGACTTGATG
ATTGAGAGA, h) rs6856130

(SEQ ID NO: 8)
TCTGTTCTGTTTTATCTGAGGCGATA[A/G]AATCCAAACGTGCAAC
TTGAACAAC,
or i) rs1372472

(SEQ ID NO: 9)
ATAAAACTCTGGTAATTCAAACCAAA[A/T]ATTTCCTCACTGAAAA
CTATGCTTG wherein the polymorphic site in each sequence is shown in bold, underlined brackets in relation to the nucleotide sequences upstream and downstream thereof. In a particularly preferred embodiment, one or more polymorphisms in the GABRA2 gene comprises rs16859227, rs279858 or both. As indicated previously, the invention also may be practiced by determining the presence or absence of the complement of the nucleotide sequence defined by the SEQ ID NOs noted above, including the complement of the polymorphic site.

The present invention also contemplates one or more polymorphisms in one or more nucleotide sequences in the GABRA2 gene which comprises between about 90% and 100% sequence identity, for example, but not limited to 90%, 91%, 92%, 93%, 94%, 95%, 96%, 97%, 98%, 99%, 99.5%, 99.9% or 100% sequence identity with SEQ ID NOs:1-9, preferably SEQ ID NOs: 1, 2 or both SEQ ID NO:1 and SEQ ID NO: 2, and wherein the sequence also comprises the respective polymorphism as shown above in bold underlined brackets. For example, but not to be considered limiting in any manner, the first nucleotide shown in SEQ ID NO:1 is a "C". The present invention is meant to include a sequence that is substantially identical to SEQ ID NO:1 but that comprises, for example, but not limited to, an "A", "G" or "T" at position number 1, as the variant nucleotide sequence exhibits more than 90% sequence identity with SEQ ID NO:1 and comprises the polymorphism shown in bold underlined brackets. The invention also may be practiced by determining the presence or absence of the complement of the nucleotide sequence defined by the SEQ ID NOs noted above, including the complement of the polymorphic site.

To determine whether a nucleic acid exhibits similarity or a percentage identity with the sequences presented herein, oligonucleotide alignment algorithms may be used, for example, but not limited to a BLAST (GenBank URL: www.ncbi.nlm.nih gov/cgi-bin/BLAST/, using default parameters: Program: blastn; Database: nr; Expect 10; filter: default; Alignment: pairwise; Query genetic Codes: Standard(1)), BLAST2 (EMBL URL: http://www.embl-heidelberg.de/Services/index.html using default parameters: Matrix BLOSUM62; Filter: default, echofilter: on, Expect: 10, cutoff: default; Strand: both; Descriptions: 50, Alignments: 50), or FASTA, search, using default parameters. Polypeptide alignment algorithms are also available, for example, without limitation, BLAST 2 Sequences (www.cbi.nlm.nih.gov/blast/bl2seq/bl2.html, using default parameters Program: blastp; Matrix: BLOSUM62; Open gap (11) and extension gap (1) penalties; gap x_dropoff: 50; Expect 10; Word size: 3; filter: default).

An alternative indication that two nucleic acid sequences are substantially complementary to each other is that the two sequences hybridize to each other under moderately stringent, or preferably stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. for at least 1 hour (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. for at least 1 hour. Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, but not wishing to be limiting, stringent conditions are selected to be about 5° C. lower than the thermal melting point for the specific sequence at a defined ionic strength and pH. The present invention also contemplates nucleotide sequences which hybridize to a nucleotide sequence comprising or consisting of SEQ ID NO:1-9, preferably SEQ ID NOs:1-2 under stringent hybridization conditions.

In a preferred embodiment, the presence of a particular allele at the polymorphic site, for example, but not limited to as provided by SEQ ID NOs: 1-2 is determined in relation to the adjacent nucleotide sequence upstream and downstream from the polymorphic site, for example, but not limited to, about 3, 4, 5, 6, 7, 8, 9, 10, 11, 12, 13, 14 or 15 nucleotides upstream and/or about 3, 4, 5, 6, 7, 8, 9, 10, 11, 12, 13, 14 or 15 nucleotides downstream of the polymorphic site. However, the present invention also contemplates that the presence of a particular allele may be determined in relation to the nucleotide sequence comprising about 20, 25, 30, 50 or more nucleotides upstream (or any number therein between) and about 20, 25, 30, 50 and/or more nucleotides downstream (or any number therein between) of the polymorphic site as provided by SEQ ID NOs: 1-9, more preferably SEQ ID NOs: 1-2, respectively. The term "and/or" is used to specifically indicate that the number of continuous upstream and downstream nucleotides does not need to be the same. Other means and methods of comparing nucleotide sequences to determine if a particular polymorphism or group of polymorphisms is present in a subject, as would be known to a person of skill in the art may be employed in the practice of the present invention.

By the term "predicting a subject's weight change in response" it is meant predicting if the subject is likely to gain weight with antipsychotic treatment in general, or with particular antipsychotic treatment, for example, but not limited to antipsychotics including clozapine and olanzapine.

In an embodiment of the present invention, but without wishing to be limiting in any manner, the method as described herein may be employed to determine a subject's weight change in response to antipsychotic medication, wherein at the time of screening the subject appears healthy. This information may be important when screening subjects that have a familial history of schizophrenia or other disorders with schizophrenic or psychotic symptoms, even though at the time of screening, the subject may have little or no symptoms of disease. Knowledge of how a subject is likely to respond to antipsychotic medication may be useful in developing treatment regimens if for example, the subject later develops schizophrenia or psychotic symptoms and requires treatment.

In an embodiment of the present invention, subjects from any ethnic race, age, gender or medical condition may be tested or screened to predict the subject's weight change in response to antipsychotic drug treatment. In this regard, a healthy subject or a subject that does not have any symptoms of a disease or medical condition may be tested to determine weight change in response to antipsychotic medication. In this way, if treatment is ever needed, a proper drug and/or treatment regimen may be selected and/or administered to the subject. In a preferred embodiment, a subject diagnosed with a disorder with one or more psychotic symptoms, schizophrenia, or schizoaffective disorder is tested to predict weight change in response to antipsychotic drug therapy, for example, but not limited to treatment with clozapine, olanzapine, risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, lurasidone, or a combination thereof.

As described above, but without wishing to be limiting in any manner, the subject is diagnosed with schizophrenia or schizoaffective disorder. However, the subject that is tested may comprise an individual with one or more psychotic symptoms, schizophrenia symptoms, schizoaffective disorder symptoms or a combination thereof, for example, but not limited to as described in DSM-IV which is hereby incorporated by reference. The psychotic symptoms may comprise positive symptoms such as, but not limited to distortions or exaggerations of inferential thinking (i.e. delusions), perception (i.e. hallucinations), language and communication (disorganized speech) and behavioral monitoring (grossly disorganized or catatonic behavior) or any combination thereof. Further, the positive symptoms may comprise distinct dimensions, for example, psychotic dimensions including, but not limited to delusions and hallucinations and disorganization dimensions including, but not limited to disorganized speech and behavior. As described previously, it is also contemplated that the symptoms may comprise one or more negative symptoms, for example, but not limited to symptoms that reflect a diminution or loss of normal function (including but not limited to, loss of motivation, loss of social interest, loss of communication, or a combination thereof). Further, the subject may exhibit a combination of both positive and negative symptoms. In an embodiment of the invention, the subject that is tested has been diagnosed or is suspected of having schizophrenia or schizoaffective disorder.

Any human tissue or sample providing genomic DNA may be used for genotyping GABRA2 polymorphisms, including but not limited to, blood, saliva, hair, spinal fluid, brain biopsy, cultured cells obtained from the subject, stool, urine, autopsy samples, or frozen sections taken for histological purposes. In certain examples, blood is obtained from a subject for assaying with respect to GABRA2 polymorphisms. As an example, but without wishing to be limiting in any manner, venous blood is obtained from a subject using standard venipuncture techniques.

The DNA of the subject may be tested for the presence or absence of the single nucleotide polymorphisms (SNPs) by any suitable technique known in the art. Representative techniques that may be employed include without limitation PCR analysis, sequencing, 5'exonuclease fluorescence assay, probe hybridization or a combination thereof.

Polymorphisms may be genotyped using conventional techniques. For example, PCR using primers incorporating fluorescent probes is one suitable technique. Further, but not wishing to be considered limiting, primers having appropriate sequences upstream and downstream of the polymorphic site may be used to amplify the nucleotide regions comprising the polymorphisms.

Single nucleotide polymorphism (SNP) analysis is useful for detecting differences between alleles of the GABRA2 gene. As described above, various methods exist in the art for genotyping nucleotide sequences including, but not limited to 5'exonuclease assays, sequencing, and the like. All such methods are meant to be encompassed herein. Further, various real-time PCR methods that can be used to detect SNPs, including, e.g., Taqman or molecular beacon-based assays (U.S. Pat. Nos. 5,210,015; 5,487,972; and PCT WO 95/13399) are useful to monitor for the presence or absence of a SNP. Still other SNP detection methods are known in the art, including, without limitation, DNA sequencing, sequencing by hybridization, dot blotting, oligonucleotide array (DNA Chip) hybridization analysis.

Applied Biosystems, Inc (Foster City, Calif.) has developed several aspects of SNP genotyping technology. In one well-used protocol, PCR amplification of a desired SNP region is conducted using targeting primers, including two allele-specific fluorogenic probes, each consisting of a different fluorescent reporter dye and a fluorescent quencher. Prior to PCR, proximity of the quencher to the fluorophore causes fluorescence resonance energy transfer (FRET), reducing the fluorescence from the reporter dye. During PCR, the 5' nuclease activity of Taq digests the allele-specific probe bound to the region of the SNP, releasing the fluorescent dye from the quencher and allowing generation of a fluorescence signal.

The method of obtaining a sample and analyzing its DNA is not critical to the present invention and any methods may be used (e.g. Ausubel, et al. (eds), 1989, Current Protocols in Molecular Biology, Green Publishing Associates, Inc., and John Wiley & Sons, Inc., New York, at p. 2.10.3, or Maniatis et al., in Molecular Cloning (A Laboratory Manual), Cold Spring Harbor Laboratory, 1982, p. 387 389). For example, which is not to be considered limiting in any manner, DNA may be extracted using a non-enzymatic high-salt procedure. Alternatively, the DNA may be analyzed in situ or present in bodily fluids and or tissues. Other methods of DNA analysis that are known to persons skilled in the art may also be used.

Several scientific collaborations have attempted to identify and/or classify SNPs for genomes of several species including *Homo sapiens, Arabidopsis thaliana, Caenorhabditis elegans, Ficedula albicollis, Ficedula hypoleuca, Gallus gallus, Mus musculus, Pan troglodytes, Plasmodium falciparum*, and *Rattus norvegicus*. For example, the HapMap project attempts to determine the common patterns of human DNA sequence variation (haplotypes). SNP genotypes, recombination rates and other types of information may be browsed at or downloaded from the HapMap website (www.hapmap.org). SNPs are typically identified by location within a nucleotide sequence, or by a database assigned reference SNP ID number ("rs" number). In addition to HapMap, SNPs may be searched using various other resources. For example, individual rs numbers of the SNPs that are known to be located in a sequence of interest may be obtained by conducting a Blast search at the UCSC Genome Bioinformatics Web Page (www.genome.ucsc.edu). Conversely, sequence and scientific literature information associated with a given rs number may be obtained by searching the dbSNP of the Entrez SNP search option provided by the NCBI web page (www.ncbi.nlm.nih gov).

In an embodiment of the present invention, which is not meant to be considered limiting, there is provided a method of predicting a subject's weight change in response to antipsychotic drug treatment comprising, a) obtaining a biological sample from the subject;
b) determining the presence or absence of one or more polymorphisms in SEQ ID NO:1, SEQ ID NO:2, or a combination thereof, wherein,
for patients of European ancestry treated with clozapine or olanzapine, the presence of the C/C genotype of the rs16859227 polymorphism (SEQ ID NO:1) is associated with a higher percentage weight gain in subjects, and;
the presence of the T/T genotype of the rs279858 polymorphism (SEQ ID NO: 2) is associated with a higher percentage weight gain in subjects, The present invention also contemplates products and kits for practicing the methods of the present invention. For example, a kit may comprise:
a) one or more primers to amplify a nucleotide sequence that comprises the polymorphism as defined in any one of SEQ ID NOs:1-9, preferably including SEQ ID NO 1 or 2, or a combination thereof;
b) one or more probes that hybridize to any one of SEQ ID NOs:1-9, preferably including SEQ ID NO:1 or 2, or both SEQ ID NO:1 and SEQ ID NO:2 over a region of nucleotides comprising the polymorphic site, wherein said probe hybridizes to a particular variant of the polymorphisms shown at the polymorphic site. Without wishing to be limiting in any manner, the probes may be labeled with an appropriate group, for example, a fluorescent tag, fluorophore, radioactive label or the like. Further, the one or more probes may be attached covalently or physically associated with a support for example, but not limited to a biochip, array, slide, multiwell plate, bead or the like. In an embodiment, which is not meant to be limiting in any manner, the probes may comprise an array of nucleic acids.

c) one or more reagents and/or products including, but not limited to, one or more buffers for performing PCR or probe hybridization, or any step in such a process as would be known to a person of skill in the art, one or more DNA amplifying enzymes, or any combination thereof;

d) one or more reagents, components and products for genotyping the polymorphisms as described herein, including, but not limited to those used in exonuclease assays, nucleotide sequencing, or any combination thereof;

e) one or more reagents, components or products for performing a DNA sequencing reaction that determines the sequence of a nucleotide sequence comprising any one of SEQ ID NOs: 1-9, preferably including SEQ ID NO:1 or 2, or both 1 and 2, or a combination thereof;

f) a gene chip or array comprising a plurality of nucleotide sequences comprising or consisting of SEQ ID NOs:1-9, preferably 1 and 2, preferably comprising nucleotide sequences only within the GABRA2 gene, and;

g) one or more sets of instructions for using the components as described herein, practicing the methods of the present invention as described herein, interpreting the data obtained from practicing the methods of the present invention or;

h) any combination thereof.

Also provided by the present invention are individual components of the kit, for example, but not limited to any product, composition described in the kit or elsewhere in the application. In a representative embodiment, the present invention provides one or more nucleic acid primers or probes.

The nucleic acid primers and probes may be of any suitable length for use in the methods of the present invention. Without wishing to be limiting in any manner, it is generally preferred that the primers and probes be between about 9 and about 100 nucleotides, for example, but not limited to about 7, 8, 9, 10, 11, 12, 13, 14, 15, 16, 17, 18, 19, 20, 21, 23, 25, 27, 29, 30, 35, 40, 45, 50, 60, 70, 80, 90, about 100 nucleotides or any amount therein between. The length of the primers and probes may also be defined by a range of any two of the values provided above or any two values therein between. With respect to probes, it is generally preferred that the probe comprise at least one, more preferably 3 or more nucleotides on each side of the polymorphic site. It is also contemplated that one or more of the primers or nucleic acid probes may be labeled as is known in the art, for example, but not limited to, with a radioactive element or tag, fluorophore, or the like.

Also provided by the present invention is a microarray, gene chip or the like which comprises one or more nucleotide sequence(s) defined by SEQ ID NOs 1-9 or a fragment thereof which comprises the polymorphic site. Preferably the microarray or gene chip comprises nucleotide sequences defined by SEQ ID NOs:1, 2 or both 1 and 2. The microarray also may comprise the complement of the nucleotide sequences or a fragment thereof which comprises the polymorphic site. Preferably, the nucleotide sequences are of a length such as, but not limited to 7, 8, 9, 10, 11, 12, 13, 14, 15, 16, 17, 18, 19, 20, 21, 22, 23, 24, 25 or more continuous nucleotides to permit strong hybridization under stringent hybridization conditions. In a preferred embodiment the microarray comprises or consists of one or more nucleotide sequences comprising polymorphic sites from the GABRA2 gene as described herein. However, the microarray may comprise additional nucleotide sequences for other genes, for example, but not limited to those involved or implicated in the diagnosis or development of schizophrenia, schizoaffective disorder or the like.

The present invention will be further illustrated in the following examples.

Examples

Clinical Diagnostic Criteria

In total, 160 participants with psychotic symptoms were included in this study. Diagnosis for schizophrenia (SCZ) was assessed by the Structured Diagnostic Interviews for DSM-IIIR and/or DSM-IV diagnoses (SCID-I,[31, 32]), except for sample A where diagnoses were based on an interview assessing both DSM and ICD diagnoses. The inclusion criteria for adult probands were DSM-IIIR/IV diagnosis of SCZ or schizoaffective disorder, with psychotic symptoms. A written informed consent was obtained after the complete study description was given to each participant, and the study has been approved by the Research Ethics Board. All subjects were self-reported as European Caucasians, and 92 of them were prescribed clozapine or olanzapine during this study period.

Subjects:

Clinical and demographic variables for the total sample of European SCZ patients (N=160) are listed in Table 1. Sample A (N=93) was collected at the Charité University Medicine, Berlin, Germany. Patients 18-60 years old diagnosed with SCZ or schizoaffective disorder according to DSM-IV and ICD-10 criteria were included. This group of patients were treated with at least one of the following medications: clozapine, haloperidol, olanzapine, risperidone, fluphenazine, aripiprazole, quetiapine, ziprasidone, and/or amisulpride (more details have been described elsewhere;[33]). Patients from Sample B (N=56) were recruited from Case Western Reserve University in Cleveland, Ohio or Hillside Hospital in Glen Oaks, N.Y. These patients received clozapine for treatment-refractoriness or intolerance to typical antipsychotic therapy according to criteria described elsewhere[34]. Clozapine serum levels were monitored during the course of the treatment to ascertain compliance. Clinical response was assessed after 6 weeks using the Brief Psychiatric Rating Scale (BPRS)[35]. Sample characterization has been described elsewhere[36]. Sample C (N=11) consists of inpatients who showed sub-optimal response to previous treatment, primarily defined by persistent positive symptoms and a poor level of functioning over the past two years. These participants were recruited at four psychiatric state hospitals (two in New York and two in North Carolina) and were randomly assigned to either clozapine or olanzapine in a 14-week, double-blinded study. Detailed clinical description of inclusion criteria, dosing schedules, assessment methods, and principal results describing antipsychotic efficacy was published elsewhere[37].

Genotyping.

Venous blood was drawn from the probands in two 10 cc EDTA tubes, and genomic DNA was extracted from blood lymphocytes using a high salt method[38]. We selected single-nucleotide polymorphisms (SNPs) based on the minimum minor allele frequency of 0.20 using HapMap genotypes (Rel 28 Phase II+III, August 10, on NCBI B36 assembly, dbSNP b126; URL: http://hapmap.ncbi.nlm.nih.gov). Specific SNPs were force-included based on previous studies. The SNPs rs279828[39-42], rs573400[39, 42, 43], rs11503014[43], rs279858 (Lys132Lys)[40, 43-46], rs16859227[43], and rs1372472[40] have been studied for possible association with alcoholism, nicotine dependence, and autism. The rs279871 marker has been associated with medial frontal brain activity in response to alcohol cue[47]. Overall, the twelve genotyped markers would provide more than 99% coverage of common variations within and 10 kb upstream and downstream of the GABRA2 gene. We narrowed the number of analyzed SNPs to nine, because the rs279858 genotypes were highly correlated to genotypes of the rs573400, rs279871, and rs279828 markers in our sample ($r^2$>0.80).

Statistical Analyses.

Statistical analyses of demographic variables, which included sex, age at recruitment, and duration of treatment, were performed across samples using Fisher's Exact tests, analysis of variance, or Kruskal-Wallis tests (Table 1). In terms of genetic analyses, the quantitative variable 'percent weight change' was analyzed using ANCOVA, with sex, treatment duration, and clozapine/olanzapine (yes/no) being included as covariates. We also analyzed the 'percent weight change' variable in a meta-analytic approach to take into account heterogeneity across the three patient sample groups using STATA version 8 (e.g.,[48]). Analyses were done with all 160 patients with available clinical/weight data, as well as secondarily with the 92 patients receiving clozapine or olanzapine, the two antipsychotics with the highest propensity for significant weight gain. Linkage disequilibrium and $r^2$ between marker pairs as determined by Haploview 4.1[49]. We also performed haplotype analysis with covariates using UNPHASED version 3.1.5[50]. We further performed an additional haplotype analysis using reconstructed haplotypes for each individual with PHASE[51]. Based on genotypic correlation among the tested SNPs, the effective number of independent markers was determined to be six; thus, we adjusted the significance threshold for multiple testing in the present study to 0.0085[52].

Results:

Table 2 presents the results from analyses of the percent weight change in antipsychotic-medicated SCZ patients of European ancestry. Genotype distributions did not deviate significantly from Hardy-Weinberg Equilibrium.

The rs279858 marker was positively associated with percent weight gain from the ANCOVA (p<0.05). More specifically, the T/T genotype was associated with higher percent weight change than the C-allele carrying genotypes (ANCOVA p=0.009). From the meta-analytic approach, the rs279858 marker (T/T homozygotes versus C allele genotype carriers) was statistically significant (z=3.80; p=1.4× $10^{-4}$). The rs1442062 marker was also significant from the meta analysis, with the A-allele carriers being associated with less weight gain than the G/G homozygotes (z=5.55; p=2.86× $10^{-8}$).

Regarding haplotypic analysis, we found a number of significant haplotypes using UNPHASED. The two-marker haplotype window across rs16859227 and rs279858 was significant (p=0.045), with the C-T haplotype associated with higher percent weight change (p=0.015; Estimated Additive Value: 0.057 [95% confidence interval: 0.011 to 0.103]). The two-marker haplotype window across rs279858 and rs1442060 was also significant (p=0.014), with the T-A haplotype associated with higher percent weight change (p=0.014; Estimated Additive Value: 0.070 [95% confidence interval: 0.014 to 0.126]) and the C-G haplotype associated with lower percent weight change (p=0.012; Estimated Additive Value: −0.115 [95% confidence interval: −0.206 to −0.0232]). On an individual level, patients with at least one copy of the (rs279858-rs1442060) T-A haplotype appeared to experience higher percentage weight gain (p=0.008; b=2.47+/−0.92), and patients with at least one copy of the (rs279858-rs1442060) C-G haplotype appeared to experience lower percentage weight gain (p=0.017; b=−2.92+/−1.21).

For patients treated with clozapine or olanzapine, the results with rs279858 were significant (ANCOVA p=0.011); these findings were similar to those from the overall sample. The meta-analysis of rs279858 across the three recruitment sites yielded statistically significant findings (z=6.71; p=$1.95 \times 10^{-11}$) that were more significant than those from the overall sample. The GABRA2 marker rs16859227 was also positive from the meta analysis (z=9.36; p=$7.97 \times 10^{-21}$), with the T-allele carriers associated with lower weight gain than C/C genotype carriers. Similarly, the rs1442062 A-allele carriers gained less weight on average than G/G homozygotes (z=5.79; p=$7.04 \times 10^{-9}$). Carriers of at least one copy of the G allele at rs11503014 gained more weight than C/C homozygotes (z=2.10; p=0.036), rs6856130 A/A homozygotes gained less weight than G-allele carriers (z=2.20; p=0.028), and rs1372472 T-allele carriers gained less weight than A/A genotype carriers (z=3.32; p=$9.0 \times 10^{-4}$).

Of all the single-marker tests, the rs279858 marker appeared to be the most consistently associated, with the T/T genotype being associated with higher percent weight gain. The two-marker haplotype window across rs16859227 and rs279858 was significant (p=0.019), with the C-T haplotype associated with higher percent weight change (p=0.011; Estimated Additive Value: 0.076 [95% confidence interval: 0.016 to 0.135]) and the T-C haplotype associated with lower percent weight change (p=0.010; Estimated Additive Value: −0.089 [95% confidence interval: −0.158 to −0.019]).

The two-marker haplotype window across rs279858 and rs1442060 was nominally significant (p=0.034), with the T-A haplotype associated with higher percent weight change (p=0.031; Estimated Additive Value: 0.075 [95% confidence interval: 0.0057 to 0.145]). On an individual level, patients with at least one copy of the (rs16859227-rs279858) C-T haplotype appeared to experience higher percentage weight gain (p=0.012; b=4.45+/−1.74). Patients with at least one copy of the (rs279858-rs1442060) T-A haplotype appeared to experience higher percentage weight gain (p=0.005; b=3.75+/−1.70).

TABLE 1

Demographic information for the study sample of European ancestry.

| Samples | A(N = 93) | B(N = 56) | C(N = 11) | p-value |
|---|---|---|---|---|
| Males/Females [d] | 56/37 | 35/21 | 11/0 | 0.037 |
| Age [a] | 32.14 ± 11.98 | 33.37 ± 7.45 | 42.15 ± 4.83 | 0.044 |
| Study duration (weeks) [a] | 5.10 ± 1.547 | 6.00 ± 0.00 | 10.55 ± 4.180 | <0.001 |
| Percentage weight change [c] | 4.00 ± 4.680 | 3.88 ± 5.770 | 5.58 ± 6.644 | 0.605 |

[c] p-value from ANOVA.
[a] p-value from Kruskal-Wallis tests.
[d] p-values from Fisher's Exact Tests.

TABLE 2

The most significant findings from analysis of the nine GABRA2 single-nucleotide polymorphisms (SNPs) in antipsychotic-induced weight gain in schizophrenia patients of European ancestry.

| SNP | Genotypes (test genotype(s) in bold) | Percentage weight change | Standard Deviation | Genotype P (all antipsychotics/ clozapine or olanzapine only) | P (all antipsychotics) Standardized Mean Difference (Confidence Interval) for rare allele-carrying genotypes | P (Clozpine/Olanzapine only) Standardized Mean Difference (Confidence Interval) for rare allele-carrying genotypes |
|---|---|---|---|---|---|---|
| rs16859227 | T/T | 5.20 | 3.99 | 0.332/0.015 | 0.091 [R] | <0.001 |
|  | T/C | 2.98 | 4.66 |  | −1.98 (−4.27, | −3.01 (−3.64, |
|  | C/C | 4.91 | 5.72 |  | 0.32) | −2.38) |
| rs279858 | T/T | 5.59 | 5.76 | 0.017/0.011 | <0.001 [R] | <0.001 |
|  | T/C | 3.63 | 4.85 |  | 2.18 (1.06, | 1.85 (1.31, |
|  | C/C | 2.72 | 5.07 |  | 3.31) | 2.39) |
| rs1442060 | A/A | 4.25 | 5.76 | 0.236/0.516 | 0.939 [R] | 0.743 [R] |
|  | A/G | 4.48 | 5.26 |  | −0.091 (−2.42, | 0.33 (−1.65, |
|  | G/G | 2.95 | 4.62 |  | 2.23) | 2.32) |
| rs3849591 | T/T | 5.11 | 5.62 | 0.893/0.629 | 0.645 [R] | 0.530 [R] |
|  | T/G | 4.42 | 5.58 |  | 0.47 (−1.52, | 0.65 (−1.38, |
|  | G/G | 3.91 | 5.16 |  | 2.45) | 2.69) |
| rs1442062 | A/A | 5.60 | 5.87 | 0.578/0.630 | <0.001 | <0.001 |
|  | A/G | 3.32 | 5.04 |  | −0.97 (−1.31, | −1.43 (−1.91, |
|  | G/G | 4.56 | 5.39 |  | −0.63) | −0.95) |

TABLE 2-continued

The most significant findings from analysis of the nine GABRA2 single-nucleotide polymorphisms (SNPs) in antipsychotic-induced weight gain in schizophrenia patients of European ancestry.

| SNP | Genotypes (test genotype(s) in bold) | Percentage weight change | Standard Deviation | Genotype P (all antipsychotics/ clozapine or olanzapine only) | P (all antipsychotics) Standardized Mean Difference (Confidence Interval) for rare allele-carrying genotypes | P (Clozpine/ Olanzapine only) Standardized Mean Difference (Confidence Interval) for rare allele-carrying genotypes |
|---|---|---|---|---|---|---|
| rs16859354 | T/T | 4.00 | 4.73 | 0.980/0.663 | 0.817 | 0.899 |
|  | T/G | 4.00 | 5.69 |  | 0.040 (−0.30, 0.38) | 0.0301 (−1.43, 0.50) |
|  | G/G | 5.16 | 4.99 |  |  |  |
| rs11503014 | G/G | 3.14 | 4.86 | 0.642/0.364 | 0.055 $^R$ | 0.036 |
|  | G/C | 4.67 | 6.00 |  | 0.754 (−0.015, 1.52) | 0.48 (0.031, 0.93) |
|  | C/C | 3.68 | 4.46 |  |  |  |
| rs6856130 | A/A | 4.07 | 5.21 | 0.289/0.097 | 0.704 $^R$ | 0.028 $^R$ |
|  | A/G | 4.49 | 5.27 |  | −0.62 (−3.80, 2.56) | −1.28 (−2.43, −0.14) |
|  | G/G | 2.42 | 5.55 |  |  |  |
| rs1372472 | T/T | 5.71 | 5.42 | 0.385/0.651 | 0.409 $^R$ | <0.001 |
|  | T/A | 3.53 | 4.77 |  | −0.55 (−1.86, 0.76) | −0.77 (−1.23, −0.32) |
|  | A/A | 4.32 | 5.69 |  |  |  |

$^c$p-values from ANCOVA of percent weight change with sex treatment duration and clozapine/olanzapine (yes/no) as covariates.
$^R$ random-effects model used.

The results provided suggest that variety of GABRA2 SNPs may be employed as genetic markers for antipsychotic weight gain.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

1. Correll C U, Sheridan E M, DelBello M P. Antipsychotic and mood stabilizer efficacy and tolerability in pediatric and adult patients with bipolar I mania: a comparative analysis of acute, randomized, placebo-controlled trials. *Bipolar Disord* 2010; 12(2): 116-141.
2. Komossa K, Depping A M, Gaudchau A, Kissling W, Leucht S. Second-generation antipsychotics for major depressive disorder and dysthymia. *Cochrane Database Syst Rev* 2010; (12): CD008121.
3. Spielmans G I, Berman M I, Linardatos E, Rosenlicht N Z, Perry A, Tsai A C. Adjunctive atypical antipsychotic treatment for major depressive disorder: a meta-analysis of depression, quality of life, and safety outcomes. *PLoS Med* 2013; 10(3): e1001403.
4. Nurmi E L, Spilman S L, Whelan F, Scahill L L, Aman M G, McDougle C J, et al. Moderation of antipsychotic-induced weight gain by energy balance gene variants in the RUPP autism network risperidone studies. *Transl Psychiatry* 2013; 3: e274.
5. Zuddas A, Zanni R, Usala T. Second generation antipsychotics (SGAs) for non-psychotic disorders in children and adolescents: a review of the randomized controlled studies. *Eur Neuropsychopharmacol* 2011; 21(8): 600-620.
6. Ballard C, Waite J. The effectiveness of atypical antipsychotics for the treatment of aggression and psychosis in Alzheimer's disease. *Cochrane Database Syst Rev* 2006; (1): CD003476.
7. Maher A R, Maglione M, Bagley S, Suttorp M, Hu J H, Ewing B, et al. Efficacy and comparative effectiveness of atypical antipsychotic medications for off-label uses in adults: a systematic review and meta-analysis. *JAMA* 2011; 306(12): 1359-1369.
8. Maher A R, Theodore G. Summary of the comparative effectiveness review on off-label use of atypical antipsychotics. *J Manag Care Pharm* 2012; 18(5 Suppl B): S1-20.
9. Arranz M J, de Leon J. Pharmacogenetics and pharmacogenomics of schizophrenia: a review of last decade of research. *Mol Psychiatry* 2007; 12(8): 707-747.
10. Muller D J, Kennedy J L. Genetics of antipsychotic treatment emergent weight gain in schizophrenia. *Pharmacogenomics* 2006; 7(6): 863-887.
11. Strange P G. Antipsychotic drugs: importance of dopamine receptors for mechanisms of therapeutic actions and side effects. *Pharmacol Rev* 2001; 53(1): 119-133.
12. Vojvoda D, Grimmell K, Sernyak M, Mazure C M. Monozygotic twins concordant for response to clozapine. *Lancet* 1996; 347(8993): 61.
13. Gebhardt S, Theisen F M, Haberhausen M, Heinzel-Gutenbrunner M, Wehmeier P M, Krieg J C, et al. Body weight gain induced by atypical antipsychotics: an extension of the monozygotic twin and sib pair study. *J Clin Pharm Ther* 2010; 35(2): 207-211.
14. Lett T A, Wallace T J, Chowdhury N I, Tiwari A K, Kennedy J L, Muller D J. Pharmacogenetics of antipsychotic-induced weight gain: review and clinical implications. *Mol Psychiatry* 2011e.
15. Cone R D. Anatomy and regulation of the central melanocortin system. *Nat Neurosci* 2005; 8(5): 571-578.
16. Hentges S T, Nishiyama M, Overstreet L S, Stenzel-Poore M, Williams J T, Low M J. GABA release from proopiomelanocortin neurons. *J Neurosci* 2004; 24(7): 1578-1583.
17. Wu Q, Palmiter R D. GABAergic signaling by AgRP neurons prevents anorexia via a melanocortin-independent mechanism. *Eur J Pharmacol* 2011; 660(1): 21-27.

18. Tong Q, Ye C P, Jones J E, Elmquist J K, Lowell B B. Synaptic release of GABA by AgRP neurons is required for normal regulation of energy balance. *Nat Neurosci* 2008; 11(9): 998-1000.
19. Soderpalm A H, Berridge K C. Food intake after diazepam, morphine or muscimol: microinjections In the nucleus accumbens shell. *Pharmacol Biochem Behav* 2000; 66(2): 429-434.
20. Cooper S J. Palatability-dependent appetite and benzodiazepines: new directions from the pharmacology of GABA(A) receptor subtypes. *Appetite* 2005; 44(2): 133-150.
21. Duke A N, Platt D M, Cook J M, Huang S, Yin W, Mattingly B A, et al. Enhanced sucrose pellet consumption induced by benzodiazepine-type drugs in squirrel monkeys: role of GABAA receptor subtypes. *Psychopharmacology (Berl)* 2006; 187(3): 321-330.
22. Ebenezer I S, Prabhaker M. The effects of intraperitoneal administration of the GABA(B) receptor agonist baclofen on food intake in CFLP and C57BL/6 mice. *Eur J Pharmacol* 2007; 569(1-2): 90-93.
23. Willer C J, Speliotes E K, Loos R J, Li S, Lindgren C M, Heid I M, et al. Six new loci associated with body mass index highlight a neuronal influence on body weight regulation. *Nat Genet* 2009; 41(1): 25-34.
24. Danovich L, Weinreb O, Youdim M B, Silver H. The involvement of GABA(A) receptor in the molecular mechanisms of combined selective serotonin reuptake inhibitor-antipsychotic treatment. *Int J Neuropsychopharmacol* 2011; 14(2): 143-155.
25. Drew K L, O'Connor W T, Kehr J, Ungerstedt U. Regional specific effects of clozapine and haloperidol on GABA and dopamine release in rat basal ganglia. *Eur J Pharmacol* 1990; 187(3): 385-397.
26. Vincent S L, Adamec E, Sorensen I, Benes F M. The effects of chronic haloperidol administration on GABA-immunoreactive axon terminals in rat medial prefrontal cortex. *Synapse* 1994; 17(1): 26-35.
27. Marx C E, VanDoren M J, Duncan G E, Lieberman J A, Morrow A L. Olanzapine and clozapine increase the GABAergic neuroactive steroid allopregnanolone in rodents. *Neuropsychopharmacology* 2003; 28(1): 1-13.
28. Ugale R R, Hirani K, Morelli M, Chopde C T. Role of neuroactive steroid allopregnanolone in antipsychotic-like action of olanzapine in rodents. *Neuropsychopharmacology* 2004; 29(9): 1597-1609.
29. Weston-Green K, Huang X F, Deng C. Alterations to melanocortinergic, GABAergic and cannabinoid neurotransmission associated with olanzapine-induced weight gain. *PLoS One* 2012; 7(3): e33548.
30. De Hert M, Yu W, Detraux J, Sweers K, van Winkel R, Correll C U. Body weight and metabolic adverse effects of asenapine, iloperidone, lurasidone and paliperidone in the treatment of schizophrenia and bipolar disorder: a systematic review and exploratory meta-analysis. *CNS Drugs* 2012; 26(9): 733-759.
31. Association AP. *Diagnostic and Statistical Manual of Mental Disorders. 4th ed. (DSM-IV).* American Psychiatric Association: Washington, D.C., 1994.
32. First M B, Gibbon M, Spitzer R L, Williams J B W. *Structured Clinical Interview for DSM-IV axis I disorders-Research Version* (SCID-I/P, version 2.0, February, Final Version). American Psychiatric Press: Washington, D.C., 1996.
33. Muller D J, Zai C C, Sicard M, Remington E, Souza R P, Tiwari A K, et al. Systematic analysis of dopamine receptor genes (DRD1-DRD5) in antipsychotic-induced weight gain. *Pharmacogenomics J* 2010e.
34. Kane J M, Honigfeld G, Singer J, Meltzer H. Clozapine in treatment-resistant schizophrenics. *Psychopharmacol Bull* 1988; 24(1): 62-67.
35. Overall J E, Gorham D R. The brief psychiatric rating scale. *Psychological Reports* 1962; 10: 799-812.
36. Masellis M, Basile V, Meltzer H Y, Lieberman J A, Sevy S, Macciardi F M, et al. Serotonin subtype 2 receptor genes and clinical response to clozapine in schizophrenia patients. *Neuropsychopharmacology* 1998; 19(2): 123-132.
37. Volavka J, Czobor P, Sheitman B, Lindenmayer J P, Citrome L, McEvoy J P, et al. Clozapine, olanzapine, risperidone, and haloperidol in the treatment of patients with chronic schizophrenia and schizoaffective disorder. *Am J Psychiatry* 2002; 159(2): 255-262.
38. Lahiri D K, Nurnberger J I, Jr. A rapid non-enzymatic method for the preparation of HMW DNA from blood for RFLP studies. *Nucleic Acids Res* 1991; 19(19): 5444.
39. Edenberg H J, Dick D M, Xuei X, Tian H, Almasy L, Bauer L O, et al. Variations in GABRA2, encoding the alpha 2 subunit of the GABA(A) receptor, are associated with alcohol dependence and with brain oscillations. *Am J Hum Genet* 2004; 74(4): 705-714.
40. Fehr C, Sander T, Tadic A, Lenzen K P, Anghelescu I, Klawe C, et al. Confirmation of association of the GABRA2 gene with alcohol dependence by subtype-specific analysis. *Psychiatr Genet* 2006; 16(1): 9-17.
41. Enoch M A. The role of GABA(A) receptors in the development of alcoholism. *Pharmacol Biochem Behav* 2008; 90(1): 95-104.
42. Haughey H M, Ray L A, Finan P, Villanueva R, Niculescu M, Hutchison K E. Human gamma-aminobutyric acid A receptor alpha2 gene moderates the acute effects of alcohol and brain mRNA expression. *Genes Brain Behav* 2008; 7(4): 447-454.
43. Agrawal A, Pergadia M L, Saccone S F, Hinrichs A L, Lessov-Schlaggar C N, Saccone N L, et al. Gamma-aminobutyric acid receptor genes and nicotine dependence: evidence for association from a case-control study. *Addiction* 2008; 103(6): 1027-1038.
44. Pierucci-Lagha A, Covault J, Feinn R, Nellissery M, Hernandez-Avila C, Oncken C, et al. GABRA2 alleles moderate the subjective effects of alcohol, which are attenuated by finasteride. *Neuropsychopharmacology* 2005; 30(6): 1193-1203.
45. Bauer L O, Covault J, Harel O, Das S, Gelernter J, Anton R, et al. Variation in GABRA2 predicts drinking behavior in project MATCH subjects. *Alcohol Clin Exp Res* 2007; 31(11): 1780-1787.
46. Ma D Q, Whitehead P L, Menold M M, Martin E R, Ashley-Koch A E, Mei H, et al. Identification of significant association and gene-gene interaction of GABA receptor subunit genes in autism. *Am J Hum Genet* 2005; 77(3): 377-388.
47. Kareken D A, Liang T, Wetherill L, Dzemidzic M, Bragulat V, Cox C, et al. A polymorphism in GABRA2 is associated with the medial frontal response to alcohol cues in an fMRI study. *Alcohol Clin Exp Res* 2010; 34(12): 2169-2178.
48. Zai G C, Zai C C, Chowdhury N I, Tiwari A K, Souza R P, Lieberman J A, et al. The role of brain-derived neurotrophic factor (BDNF) gene variants in antipsychotic response and antipsychotic-induced weight gain. *Prog Neuropsychopharmacol Biol Psychiatry* 2012; 39(1): 96-101.

49. Barrett J C, Fry B, Maller J, Daly M J. Haploview: analysis and visualization of LD and haplotype maps. *Bioinformatics* 2005; 21(2): 263-265.
50. Dudbridge F. Likelihood-based association analysis for nuclear families and unrelated subjects with missing genotype data. *Hum Hered* 2008; 66(2): 87-98.
51. Stephens M, Smith N J, Donnelly P. A new statistical method for haplotype reconstruction from population data. *Am J Hum Genet* 2001; 68(4): 978-989.
52. Li J, Ji L. Adjusting multiple testing in multilocus analyses using the eigenvalues of a correlation matrix. *Heredity* (*Edinb*) 2005; 95(3): 221-227.

What is claimed is:

1. A method for treating a subject in need thereof with an antipsychotic drug in a manner that reduces the subject's risk of weight gain in response to treatment with the antipsychotic drug, the method comprising
   a) determining the subject's genotype, at one or more genetic markers selected from the group consisting of rs279858 (T/T), rs1442062 (G/G), rs16859227 (C/C), rs11503014 (G/C, G/G), rs6856130 (G/A, G/G), rs1372472 (A/A) by a method comprising PCR analysis, sequencing, 5' exonuclease fluorescence assay, probe hybridization, or a combination thereof;
   b) identifying the subject as being at increased risk of weight gain in response to treatment with an antipsychotic drug where the subject's genotype matches one or more genotypes selected from the group consisting of:
      rs279858 (T/T),
      rs1442062 (G/G),
      rs16859227 (C/C),
      rs11503014 (G/C, G/G),
      rs6856130 (G/A, G/G), and
      rs1372472 (A/A);
   and
   c) administering to the subject identified in b) an antipsychotic drug selected from the group consisting of paliperidone, perphenazine, thioridazine, chlorpromazine, risperidone and quetiapine.

2. The method of claim 1, wherein step a) comprises determining the subject's genotype for at least two of the genetic markers.

3. The method of claim 2, wherein step a) comprises determining the subject's genotype for rs16859227 and rs279858 and step b) comprises identifying the subject as at increased risk of weight gain in response to treatment with an antipsychotic drug where the subject's genotype is C/C at rs16859227 and comprises a T at rs279858.

4. The method of claim 2, wherein step a) comprises determining the subject's genotype for rs279858 and further comprises determining the subject's genotype for rs1442060 and step b) comprises identifying the subject as at increased risk of weight gain in response to treatment with an antipsychotic drug where the subject's genotype is T/T at rs279858 and further comprises an A at rs1442060.

5. The method of claim 1, wherein step a) comprises determining the subject's genotype for rs279858 and step b) comprises identifying the subject as at increased risk of weight gain in response to treatment with an antipsychotic drug where the subject's genotype is T/T at rs279858.

6. The method of claim 1, wherein the method further comprises determining a treatment regimen for the subject that avoids clozapine and olanzapine for the subject at increased risk of weight gain.

7. The method of claim 1, wherein the method further comprises determining a treatment regimen for the subject that includes an antipsychotic selected from loxapine, iloperidone, asenapine, lurasidone, ziprasidone, aripiprazole, fluphenazine, and haloperidol for the subject at increased risk of weight gain.

8. The method of claim 1, wherein the subject is human.

9. The method of claim 2, wherein step a) comprises determining the subject's genotype for rs16859227 and rs279858 and step b) comprises identifying the subject as at increased risk of weight gain in response to treatment with an antipsychotic drug where the subject's genotype comprises a C at rs16859227 and is T/T at rs279858.

* * * * *

```
                            SEQUENCE LISTING

<160> NUMBER OF SEQ ID NOS: 9

<210> SEQ ID NO 1
<211> LENGTH: 53
<212> TYPE: PRT
<213> ORGANISM: homo sapien

<400> SEQUENCE: 1

Cys Cys Thr Thr Gly Gly Thr Thr Thr Thr Ala Thr Ala Cys Ala Ala
1               5                   10                  15

Gly Cys Ala Thr Gly Cys Ala Ala Ala Gly Cys Thr Ala Thr Ala Thr
            20                  25                  30

Ala Ala Thr Ala Gly Ala Ala Thr Cys Ala Cys Ala Thr Gly Gly Ala
        35                  40                  45

Ala Ala Cys Ala Ala
    50

<210> SEQ ID NO 2
<211> LENGTH: 53
<212> TYPE: PRT
<213> ORGANISM: homo sapien

<400> SEQUENCE: 2

Ala Thr Thr Gly Thr Cys Ala Thr Ala Thr Thr Ala Thr Gly Ala Gly
1               5                   10                  15

Cys Thr Ala Cys Thr Gly Ala Thr Thr Thr Cys Thr Thr Cys Cys
            20                  25                  30

Cys Ala Thr Thr Gly Thr Gly Ala Ala Ala Ala Ala Gly Gly Thr
        35                  40                  45

Ala Thr Cys Thr Gly
    50

<210> SEQ ID NO 3
<211> LENGTH: 53
<212> TYPE: PRT
<213> ORGANISM: homo sapien

<400> SEQUENCE: 3

Gly Thr Ala Ala Ala Gly Thr Gly Thr Cys Ala Cys Ala Thr Cys Ala
1               5                   10                  15

Ala Thr Gly Cys Cys Ala Thr Ala Thr Cys Ala Gly Thr Ala Thr Thr
            20                  25                  30

Cys Thr Gly Thr Ala Gly Ala Thr Gly Gly Cys Ala Thr Gly Thr Thr
        35                  40                  45

Ala Thr Cys Ala Thr
    50

<210> SEQ ID NO 4
<211> LENGTH: 53
<212> TYPE: PRT
<213> ORGANISM: homo sapien

<400> SEQUENCE: 4

Cys Thr Cys Ala Thr Thr Thr Cys Cys Thr Thr Gly Cys Thr Thr Cys
```

```
                1               5                  10                  15
Thr Ala Ala Gly Gly Thr Ala Gly Gly Gly Thr Thr Cys Ala Thr
                    20                  25                  30
Cys Ala Ala Thr Thr Thr Ala Thr Cys Thr Ala Thr Cys Thr Cys Ala
                    35                  40                  45
Thr Gly Gly Gly Ala
    50
```

<210> SEQ ID NO 5
<211> LENGTH: 53
<212> TYPE: PRT
<213> ORGANISM: homo sapien

<400> SEQUENCE: 5

```
Gly Ala Gly Ala Ala Gly Gly Thr Gly Ala Ala Thr Ala Gly Ala
1               5                  10                  15
Thr Thr Thr Ala Ala Cys Thr Cys Ala Thr Ala Gly Thr Ala Thr Cys
                    20                  25                  30
Ala Ala Ala Thr Thr Ala Ala Gly Ala Thr Thr Gly Cys Ala Cys Cys
                    35                  40                  45
Thr Thr Ala Ala Ala
    50
```

<210> SEQ ID NO 6
<211> LENGTH: 53
<212> TYPE: PRT
<213> ORGANISM: homo sapien

<400> SEQUENCE: 6

```
Thr Ala Cys Ala Ala Thr Ala Thr Cys Thr Thr Gly Ala Cys Thr Cys
1               5                  10                  15
Ala Ala Thr Gly Ala Gly Cys Thr Thr Cys Gly Thr Ala Ala Thr Cys
                    20                  25                  30
Thr Thr Ala Ala Thr Ala Ala Gly Gly Thr Ala Ala Cys Ala Ala Gly
                    35                  40                  45
Ala Gly Ala Ala Ala
    50
```

<210> SEQ ID NO 7
<211> LENGTH: 53
<212> TYPE: PRT
<213> ORGANISM: homo sapien

<400> SEQUENCE: 7

```
Ala Ala Gly Cys Thr Ala Thr Gly Gly Ala Gly Ala Thr Thr Ala Cys
1               5                  10                  15
Thr Thr Cys Cys Thr Gly Gly Ala Cys Thr Cys Gly Thr Gly Thr Gly
                    20                  25                  30
Thr Ala Gly Gly Ala Cys Thr Thr Gly Ala Thr Gly Ala Thr Thr Gly
                    35                  40                  45
Ala Gly Ala Gly Ala
    50
```

<210> SEQ ID NO 8
<211> LENGTH: 53
<212> TYPE: PRT
<213> ORGANISM: homo sapien

<400> SEQUENCE: 8

-continued

```
Thr Cys Thr Gly Thr Thr Cys Thr Gly Thr Thr Thr Ala Thr Cys
1               5                   10                  15

Thr Gly Ala Gly Gly Cys Gly Ala Thr Ala Ala Gly Ala Ala Thr Cys
            20                  25                  30

Cys Ala Ala Ala Cys Gly Thr Gly Cys Ala Ala Cys Thr Thr Gly Ala
                35                  40                  45

Ala Cys Ala Ala Cys
        50

<210> SEQ ID NO 9
<211> LENGTH: 53
<212> TYPE: PRT
<213> ORGANISM: homo sapien

<400> SEQUENCE: 9

Ala Thr Ala Ala Ala Ala Cys Thr Cys Thr Gly Gly Thr Ala Ala Thr
1               5                   10                  15

Thr Cys Ala Ala Ala Cys Cys Ala Ala Ala Thr Ala Thr Thr Thr
            20                  25                  30

Cys Cys Thr Cys Ala Cys Thr Gly Ala Ala Ala Cys Thr Ala Thr
        35                  40                  45

Gly Cys Thr Thr Gly
        50
```